(12) United States Patent
Touzawa et al.

(10) Patent No.: US 6,839,456 B2
(45) Date of Patent: Jan. 4, 2005

(54) SYSTEM FOR ACCURATELY OBTAINING A CONTOUR AND/OR QUANTITATIVE INFORMATION FROM AN ECHO IMAGE WITH REDUCED MANUAL OPERATION

(75) Inventors: Yoshito Touzawa, Toyama (JP); Morio Nishigaki, Fujisawa (JP); Hisashi Hagiwara, Yokohama (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 10/454,638

(22) Filed: Jun. 5, 2003

(65) Prior Publication Data

US 2003/0198372 A1 Oct. 23, 2003

Related U.S. Application Data

(62) Division of application No. 09/408,101, filed on Sep. 29, 1999, now Pat. No. 6,687,392.

(30) Foreign Application Priority Data

Sep. 30, 1998 (JP) .......................................... 10-291351

(51) Int. Cl.$^7$ ............................. G06K 9/00; G06K 9/46; G06K 9/52; G06K 9/40

(52) U.S. Cl. ....................... 382/128; 382/203; 382/206; 382/266

(58) Field of Search ............................... 382/128, 130, 382/131, 132, 190, 195, 203, 154, 199, 206, 266, 256, 300; 345/427, 442, 585

(56) References Cited

U.S. PATENT DOCUMENTS

| 4,620,287 A | 10/1986 | Yam ............................. 345/442 |
| 4,791,581 A | 12/1988 | Ohba ........................... 345/585 |
| 5,107,838 A | 4/1992 | Yamaguchi |
| 5,235,985 A | 8/1993 | McMorrow et al. |
| 5,559,901 A | 9/1996 | Lobregt ....................... 382/256 |
| 5,871,019 A * | 2/1999 | Belohlavek .................. 600/450 |
| 5,872,571 A * | 2/1999 | Arling ......................... 345/427 |
| 6,201,888 B1 | 3/2001 | Kalvin ........................ 382/131 |
| 2001/0024516 A1 * | 9/2001 | Yoshioka et al. ........... 382/128 |

FOREIGN PATENT DOCUMENTS

| JP | 07246207 | 9/1995 | |
| JP | 8-89503 | 4/1996 | |
| JP | 8-299341 | 11/1996 | |
| JP | 10-099328 | * 4/1998 | ............ A61B/8/00 |

OTHER PUBLICATIONS

Coppini et al, "Recovery of the 3–D Shape of the Left Ventricle from Echocardiographic Images", Jun. 1995, IEEE Transaction on Medical Imaging, vol. 14, No. 2, pp. 301–317.*

(List continued on next page.)

Primary Examiner—Mehrdad Dastouri
(74) Attorney, Agent, or Firm—Louis Woo

(57) ABSTRACT

A system for analyzing an echo image containing a contour of an organ with reduced manual operation is provided. The echo image is first obtained. A user manually sets, say, four points as known or initial points such that two of the known points provide a width of the contour and the other two of the known points provide a height of the contour. A search region including a connecting line segment connecting each pair of adjacent ones of the known points is set on the contour. A search line segment that originates from a point bisecting the connecting line segment of the search region and reaches an end of the search region is set. Each search line segment is sought for a contour point constituting the contour. A contour is formed by connecting the contour points on the search line segments. Three points may be set as the initial points such that two of the initial points provide a width of the contour and the other one is on top of the contour.

2 Claims, 15 Drawing Sheets

OTHER PUBLICATIONS

Wilson DC, Geiser EA, Conetta DA, Murphy JM, Wang D: "An Automated Algorithm for Analysis of 2–D Echocardiographic Short–Axis Images: A Brief Overview" Proceedings MMBIA '96, 1996, pp. 222–231, XP002258079.

Geiser E A et al: "A Second–Generation Computer–Based Edge Detection Algorithm for Short–Axis, Two–Dimensional Echocardiographic Images: Accuracy and Improvement in Interobserver variability" Journal of the American Society of Echocardiography, Mosby–Year Book, Inc. St. Louis, MO, US, vol. 3, No. 2, Mar. 1, 1990, pp. 79–90, XP000576412 ISSN: 0894–7317.

Tamura S et al: "Plan–Based Boundary Extraction and 3–D Reconstruction for orthogonal 2–D Echocardiography" Pattern Recognition, vol. 20, No. 2, 1987, pp. 155–162, XP009018444.

Petit E et al: "Estimation Des Volumes Ventriculaires Gauches Par Detection Et Suivi Automatiques De Contours Sur Des Sequences D'Images Echocardiographiques. Left Ventricular Volume Assessment By Automated Border Tracking on Echocardiographic Image Sequences" Onde Electrique, Editions Chiron S. A. Paris, FR, vol. 71, No. 4, Jul. 1, 1991, pp. 41–44, XP000243164 ISSN: 0030–2430.

S.K. Setarehdan et al., "Cardiac left ventricular volume changes assessment by long axis echocardiographical image processing", IEE Proceedings: Vision, Image and Signal Processing, Institution of Electrical Engineers, GB, vol. 145, No. 3, Jun. 1, 1998, pp. 203–212.

* cited by examiner

INITIAL CONTOUR POINTS (REFERENCE CONTOUR POINTS FOR SEARCH CYCLE 1)

SEARCH CYCLE 1

REFERENCE CONTOUR POINTS FOR SEARCH CYCLE 2

SEARCH CYCLE 2

□ : REFERENCE CONTOUR POINT THAT HAS BEEN OBTAINED BEFORE THE CURRENT SEARCH CYCLE.

■ : CONTOUR POINT TO BE OBTAINED IN THE CURRENT SEARCH CYCLE.

FIG. 3

| SEARCH CYCLE i | THE NUMBER OF CONTOUR POINTS | | |
|---|---|---|---|
| | OBTAINED BY THE END OF THE LAST SEARCH CYCLE (REFERENCE POINTS) | TO BE OBTAINED IN THIS SEARCH CYCLE $L_i (=4*2^{i-1})$ | OBTAINED BY THE END OF THIS SEARCH CYCLE |
| 1 | 4 INITIAL POINTS | 4 | 8 |
| 2 | 8 | 8 | 16 |
| 3 | 16 | 16 | 32 |
| ...... | ...... | ...... | ...... |
| i | $L_i$ | $L_i$ | $2*L_i (=4*2^i)$ |
| ...... | ...... | ...... | ...... |
| L | $4*2^{L-1}$ | $4*2^{L-1}$ | $4*2^L$ |

STEP 136 IN SEARCH CYCLE i

NEXT SEARCH CYCLE i+1

CORRECTION BY INTERPOLATION JUST AFTER THE NEXT SEARCH CYCLE i+1

■ INITIAL CONTOUR POINT

□ EXTRACTED CONTOUR POINT $k = -L, \cdots, 0, \cdots, K$

US 6,839,456 B2

SYSTEM FOR ACCURATELY OBTAINING A CONTOUR AND/OR QUANTITATIVE INFORMATION FROM AN ECHO IMAGE WITH REDUCED MANUAL OPERATION

This is a divisional of application Ser. No. 09/408,101, filed Sep. 29, 1999, now U.S. Pat. No. 6,687,392

BACKGROUND OF THE INVENTION

1. Field of the Invention

The invention relates to an image processing system and more particularly to a method of and system for quantitatively analyzing input image(s) of an object given as an input image and in particular ultrasonic video image(s). The quantitative analysis includes the 2-D and 3-D contour extraction of the object, the calculation of the area enclosed by the 2-D contour at a slice position in the object and the calculation of volume of the body.

2. Description of the Prior Art

Japanese unexamined patent publication Hei10-99,328 (1998) discloses a ultrasonic diagnostic system for accurately recognizing and automatically obtaining the time period of the contraction last period and expansion last period of the heart.

Japanese unexamined patent publication Hei8-299,341 (1996) discloses an ultrasonic volume calculation device. Only voxels (volume cells) having link to the reference voxel out of voxels whose binary processing results are value to be extracted are separated and extracted by executing link determination operation for the binary processing results of the respective voxels so as to be set as a target region. The volume is calculated by counting the voxels in the target region.

However, conventional contour extracting system searches a wide area for contour points without limiting the search area by using information on shapes of the contour of a target organ. This may cause wrong position to be counted as true contour points due to noise or unclearness of the echo image.

It is an object of the invention to provide a method of and a system for extracting a contour of an object given as an input image and/or calculating the area or volume enclosed by the contour with a high precision, through reduced manual operation.

SUMMARY OF THE INVENTION

According to one aspect of the invention, a method of analyzing an echo image containing a contour of an organ with reduced manual operation is provided. The method includes the steps of: obtaining the echo image; (1) setting a search region including a connecting line segment connecting each pair of adjacent ones of known points on the contour; (2) setting a search line segment that originates from a point bisecting the connecting line segment of the search region and reaches an end of the search region; (3) searching each search line segment for a contour point constituting the contour; and forming the contour by connecting the contour points on the search line segments.

In one embodiment, a user manually sets four points as the known or initial points such that two of the known points provide a width of the contour and the other two of the known points provide a height of the contour.

In another embodiment, three points are set as the known or initial points such that two of the known points provide a width of the contour and the other one of the known points is on top of the contour.

According to another aspect of the invention, a method for obtaining an approximated three-dimensional contour and/or quantitative information from at least two echo images intersecting each other is provided. The method includes the steps of: specifying two points that lie on an intersecting line made by the at least two echo images and on the contour; specifying, on each echo image, two contour point providing a maximum length in a direction perpendicular to the intersecting line; extracting a contour of the organ in each echo image; setting a plurality of equally-spaced border approximation planes perpendicular to the intersecting line; and approximating a border of the organ based on intersecting points made by each border approximation plane intersecting the intersecting line and the extracted contours.

BRIEF DESCRIPTION OF THE DRAWING

The features and advantages of the present invention will be apparent from the following description of an exemplary embodiment of the invention and the accompanying drawing, in which:

FIG. 3 is a table showing the number of contour points obtained in each search cycle;

Throughout the drawing, the same elements when shown in more than one figure are designated by the same reference numerals.

DETAILED DESCRIPTION OF THE PREFERRED EMBODIMENTS

Figure 1:
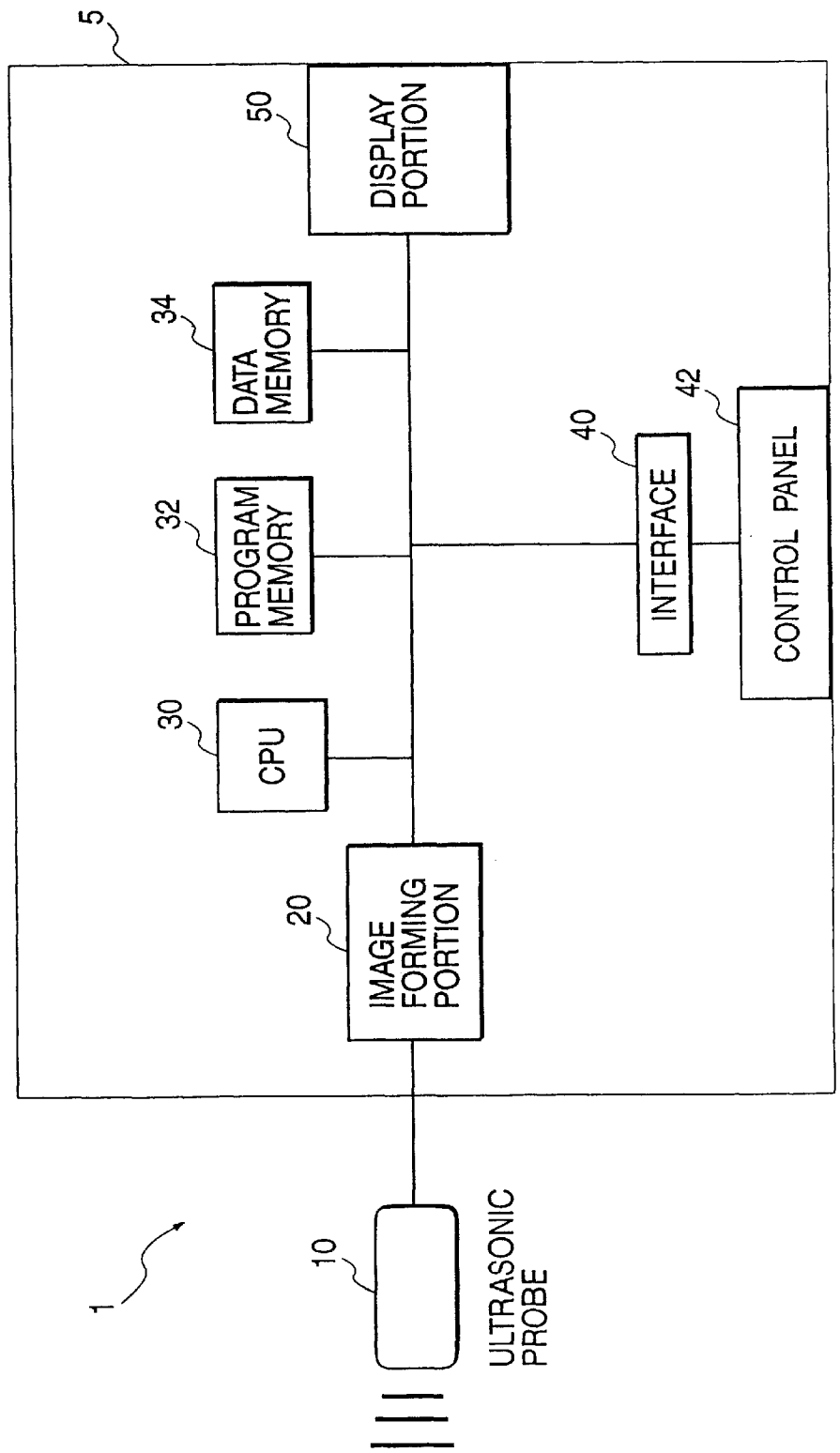
FIG. 1 is a diagram showing an arrangement of an ultrasonic diagnostics system 1 for quantitatively analyzing echo image(s) of an internal organ in accordance with one of embodiments of the present invention.

FIG. 1 is a diagram showing an arrangement of an ultrasonic diagnostics system 1 for quantitatively analyzing echo image(s) of an object such as an internal organ in accordance with one of embodiments of the present invention detailed in the following. In FIG. 1, the ultrasonic diagnostics system 1 comprises an ultrasonic probe 10 for transmitting an ultrasonic wave and for receiving a reflected echo wave and a main body 5 for forming a tomographic echo image from the received echo wave and for providing the 2-D and 3-D contour extraction of the internal organ, the calculation of the area enclosed by the 2-D contour at a slice position in the organ and the calculation of volume of the organ.

The main body 5 is provided with an ultrasonic wave generator/image forming portion 20 for generating the ultrasonic wave and for receiving an echo wave and forming an echo image. It is noted that the ultrasonic probe 10 and the ultrasonic wave generator/image forming portion 20 may be either configured to provide a 2D image or configured to provide a 3D image.

Excepting the ultrasonic wave generator/image forming portion 20, the main body 5 is basically a computer comprising a CPU (central processing unit) 30, a program memory 32, a data memory 34, a control panel (or console) 40 and a display portion 50.

The control panel 40 may be either a conventional keyboard or a tailored control panel. The data memory 34 includes RAM (random access memory) and a mass storage such as a hard disc and stores tomographic images formed by the portion 20 and various data used in the processing by the CPU 30. The program memory 32 stores programs that realize various functions of the ultrasonic diagnostics system 1 in accordance with one of the following embodiments of the invention.

Contour Extraction

Referring to FIGS. 2 and 3, a basic concept of the invention will be described. FIG. 2 is a diagram showing how the contour points are obtained in accordance with a first illustrative embodiment of the invention. FIG. 3 is a table showing the number of contour points obtained in each search cycle (detailed later).

Figure 2A:
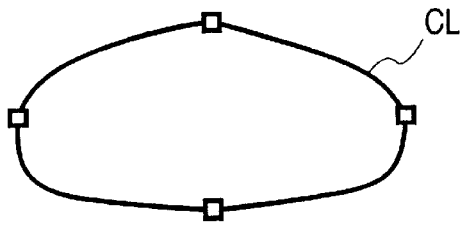
FIG. 2 is a diagram showing how the contour points are obtained in accordance with a first illustrative embodiment of the invention.
Figure 2B:
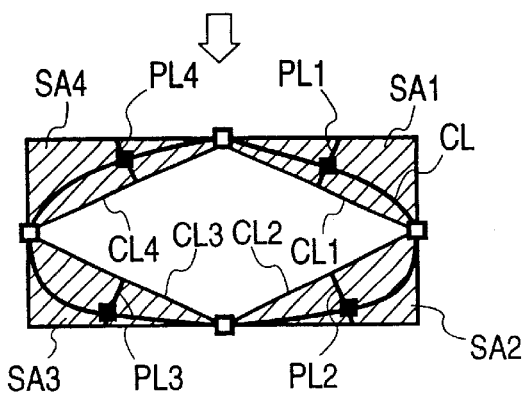
Figure 2C:
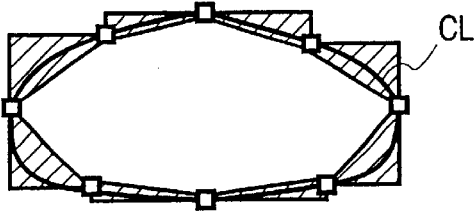
Figure 2D:
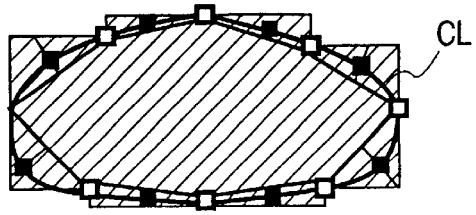

According to the first embodiment of the invention, a predetermined number of contour points (four points in this example) on a contour line of the internal organ (shown as "CL" in FIG. 2A) are first specified manually by the user as shown in FIGS. 2A and 3. Then, based on the initial contour points, contour points that are the same in number as the initial contour points are searched in the first search cycle as shown in FIG. 2B. That is, eight contour points are obtained by the end of the first search cycle. Since, the contour points having been obtained so far, i.e., the eight contour points shown as small white-on-black squares in FIG. 2C enable the calculation of further contour points of the same number as the so-far-obtained contour points in the next or second search cycle, the so-far-obtained contour points or the eight contour points are referred to as "reference contour points" for the next or second search cycle. Thus, eight new contour points shown as small squares filled with black in FIG. 2D are obtained based on the eight reference contour points of FIG. 2C in the second search cycle.

In this way, in an i-th search cycle (i=1, 2, . . . ), Li contour points are obtained based on Li reference contour points having been obtained by the search cycle (i-1), where Li equals 4*2-1. Completion of the search cycle i yields $2*Li(=4*2^i)$ contour points. In FIG. 3, the number of search cycles is set to L. Thus, completion of the entire search cycles yields $4*2^L$ contour points.

Figure 4:
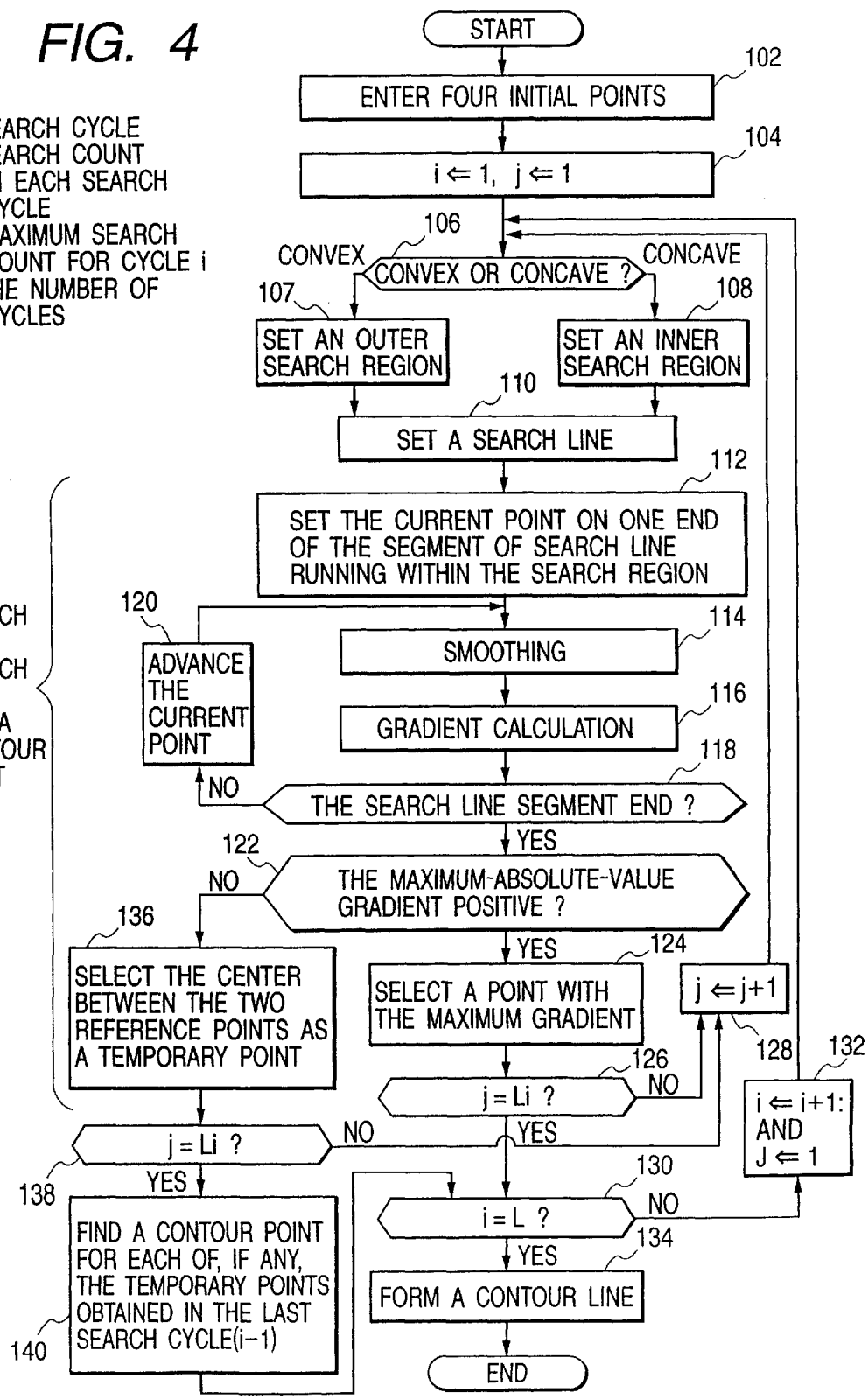
FIG. 4 is a flowchart showing an operation of extracting a contour of an internal organ in an echo image.

FIG. 4 is a flowchart showing an operation of extracting a contour of an internal organ in an echo image. The operation is executed by the CPU 30 under the control of a program stored in the program memory 32. In FIG. 4, step 102 lets the user specify a predetermined number (four in this specific example) of points (hereinafter referred to as "contour points") on the contour line CL drawn in an given echo image as shown in FIG. 2A, and proceeds to step 104. Step 104 sets both a search cycle counter i and a contour point counter j (a counter for the contour points to be obtained in each search cycle) for an initial value "1".

If the contour points are calculated from one just following a certain reference contour point counted counterclockwise, then a counter point "j" to be obtained is the 2*j-th contour points from the above reference counter point when counted including reference contour points. For this reason, a j-th contour point to be obtained is hereinafter denoted as "$P_{2j}$". Also, the adjacent reference points used for obtaining the contour point $P_{2j}$ are denoted as "$P_{2j-1}$" and "$P_{2j+1}$" in the counterclockwise order.

After step 104, CPU 30 proceeds to step 106. Step 106 determines whether the part of the contour line where a new contour point is searched for is convex or concave according to known contour points.

Figure 5:
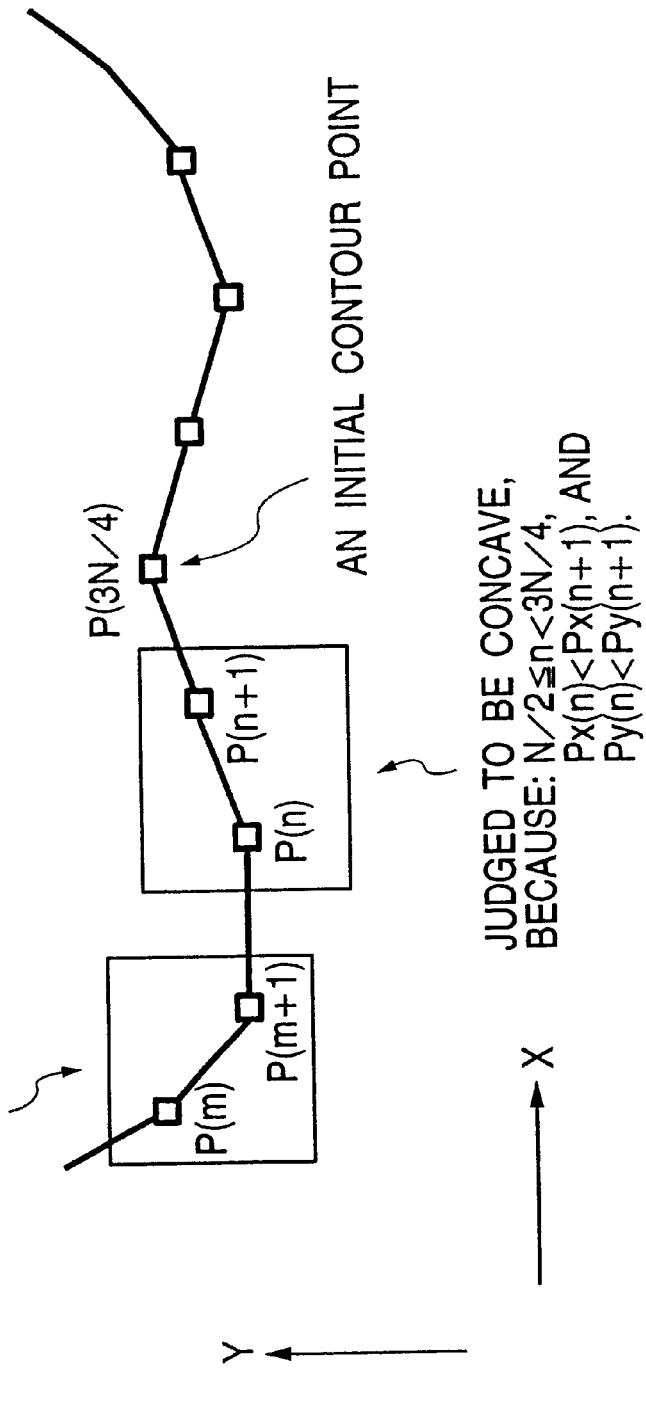
FIG. 5 is a diagram illustrating how the local shape of the contour line is determined.

FIG. 5 is a diagram illustrating how the local shape of the contour line is determined. In FIG. 5, "N" indicates the number of contour points. P(n) and P(n+1) are n-th and (n+1)-th contour points when counted counterclockwise from a rightmost initial contour point. The initial contour points are expressed as P(1) (not shown), P(N/4) (not shown), P(N/2) (not shown) and P(3N/4). In the following discussion, the X and Y coordinates of the point P(n) is denoted as Px(n) and Py(n), respectively.

A section of the contour line CL located between P(n) and P(n+1) is judged to be concave if any of the following conditions is satisfied.

(1) $1 \leq n < N/4$, $Px(n) > Px(n+1)$ and $Py(n) > Py(n+1)$.
(2) $1 \leq n < N/2$ and $Px(n) < Px(n+1)$.
(3) $N/4 \leq n < N/2$, $Px(n) > Px(n+1)$ and $Py(n) < Py(n+1)$.
(4) $N/2 \leq n < N$, $Py(n) > Px(n+1)$.
(5) $N/2 \leq n < 3N/4$, $Px(n) < Px(n+1)$ and $Py(n) < Py(n+1)$.
(6) $3N/4 \leq n < N$, $Px(n) < Px(n+1)$ and $Py(n) > Py(n+1)$.

In FIG. 5, the section between points P(n) and P(n+1) is judged to be concave because the points P(n) and P(n+1) satisfy the condition (5). However, the section between points P(m) and P(m+1) is not judged to be concave because the points P(m) and P(m+1) do not satisfy any of the above conditions.

In the above description, the convex/concave judgement is made by using the X and Y coordinates. However, the judgement may be made by using polar coordinates of adjacent reference contour points and examining the distances of the adjacent reference contour points.

Though the convex/concave judgement has been made based on a positional relationship between two adjacent contour points in the above description, the judgement may be made by using three consecutive contour points.

If the section in question is judged to be convex in step 106, the control is passed to step 107. Step 107 sets an outer search area. Turning back to FIG. 2B, lines CL1 through CL4 are connecting lines that connects adjacent reference contour points. Areas SA1 through SA4 are search areas set for the contour points $P_{2 \times 1}$, $P_{2 \times 2}$, $P_{2 \times 3}$ and $P_{2 \times 4}$. Lines PL1 through PL4 are lines substantially perpendicular to the connecting lines CL1 through CL4, respectively. It is assumed that the above described initial contour points are so selected that two of them substantially provide the maximum width of the internal organ and the other two of them substantially provide the maximum height of the organ. If the ultrasonic diagnostics system 1 is applied to organs with a basically convex shape such as the heart, the prostate, etc., then it can be said that the section of the contour line CL that is located between two adjacent reference contour points lies within the right-angled triangle having the two reference contour points as two of its vertices.

Figure 6:
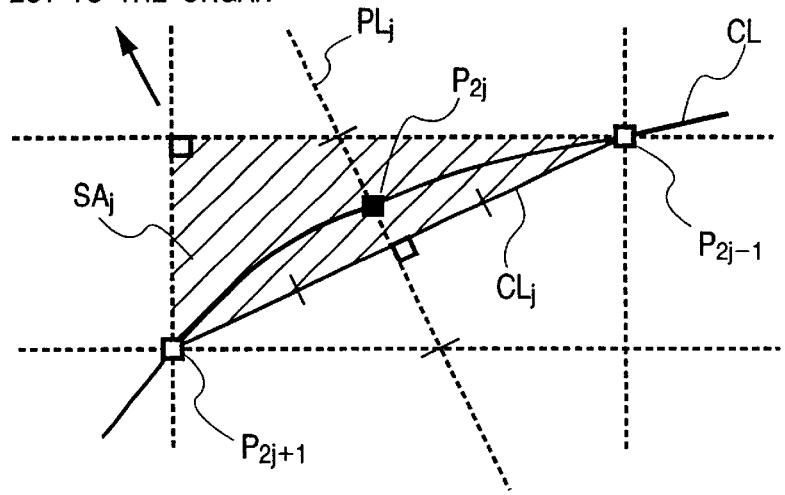
FIG. 6 is a diagram showing the way of setting a search area and a search line for a j-th contour point to be obtained, i.e., a contour point $P_{2j}$ if a section of the contour line CL including the point $P_{2j}$ is convex.

FIG. 6 is a diagram showing the way of setting a search area and a search line for a j-th contour point to be obtained, i.e., a contour point $P_{2j}$ if a section of the contour line CL including the point $P_{2j}$ is convex. In FIG. 6, step 107 sets a search area SAj by connecting adjacent reference points $P_{2j-1}$ and $P_{2j+1}$ with a line CLj and selecting a right-angled triangle that has the line CLj as its one side and has the right angle outside the organ. In other words, the search area SAj is a right-angled triangle formed by the connecting line CLj, and lines that pass the reference points $P_{2j-1}$ and $P_{2j+1}$ and parallel the horizontal and vertical axes as shown in FIG. 6.

Figure 7:
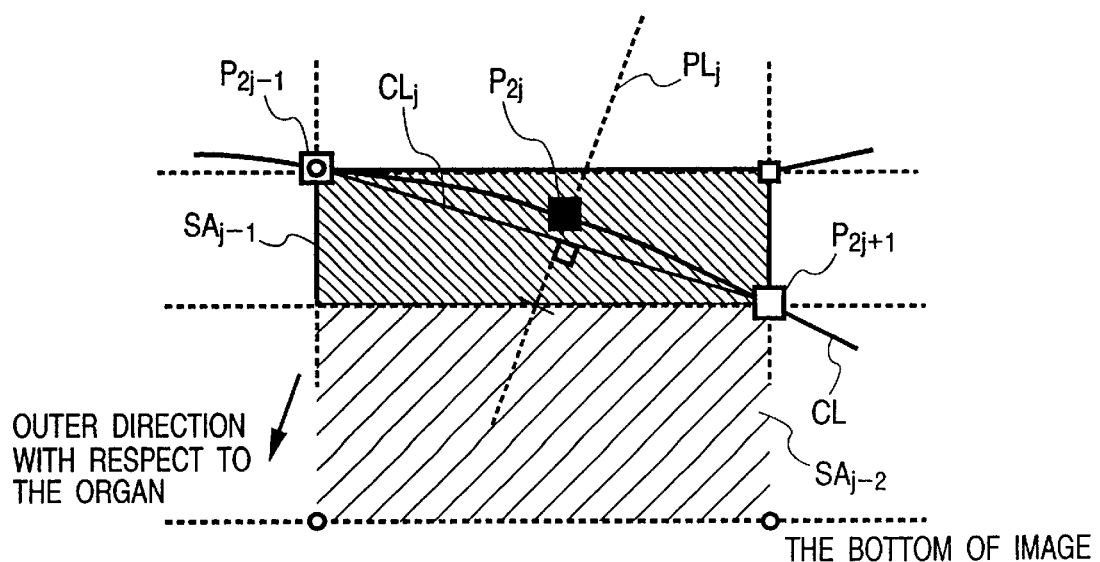
FIG. 7 is a diagram showing the way of setting a search area and a search line for a j-th contour point to be obtained, i.e., a contour point $P_{2j}$ if a section of the contour line CL including the point $P_{2j}$ is concave.

If the section in question is judged to be concave in step 106, the control is passed to step 108. Step 108 sets an inner search area. FIG. 7 is a diagram showing the way of setting a search area and a search line for a j-th contour point to be obtained, i.e., a contour point $P_{2j}$ if a section of the contour line CL including the point $P_{2j}$ is concave. In FIG. 7, step 108 at least sets a rectangular search area SAj-1. Step 108 may set an enlarged search area comprising the area SAj-1 and an area SAj-2 whose lower limit is the bottom of the echo image if the point $P_{2j+1}$ is on the left of the point $P_{2j+1}$ as shown in FIG. 7. If the point $P_{2j-1}$ is on the right of the point $P_{2j+1}$, then step 108 may set an enlarged search area comprising the area SAj-1 and an area SAj-2 whose upper limit is the top of the echo image.

Though we have listed 6 cases in which a section of the contour line CL located between P(n) and P(n+1) is judged to be concave, if there is a section of the contour line CL that is considered to be concave even if the section falls on none of the six cases, then an arrangement by the user or a preset is preferably made such that a rectangular search area is set as shown as SAj-1 and/or SAj-2 in FIG. 7.

A rectangular search area has been set through either a decision by the user based on the positional relationship between adjacent reference points or a setting by the user. An arrangement may be made such that a rectangular search area is always set for a section that is expected in advance to be concave due to a transformation by a pressure of the ultrasonic probe 10.

After step 107 or 108, the control is passed to step 110. Step 110 sets a search line segment PLj which intersects substantially perpendicularly with the connecting line CLj connecting adjacent reference points $P_{2j-1}$ and $P_{2j+1}$ at the center of the line CLj and lies within the search area SAj as shown in FIG. 6 or 7. Then, step 112 sets the current search point on one end of the search line segment PLj. Through steps 114 through 124 and step 136, the search line segment PLj is searched for a contour point.

Step 114 performs a smoothing operation based on the values of pixels on the search line segment PLj and peripheral pixels along the line segment PLj to obtain noise-reduced pixel values. The smoothing operation is achieved by using a convolution kernel based on, for example, a Gauss function to perform a convolution on the convolution kernel and the peripheral pixels. In the smoothing operation, all that has to be obtained is only pixels necessary for the calculation of gradient at each of the pixels on the search line segment PLj.

Following step 114, step 116 calculates the gradient at each pixel of the line segment PLj to obtain a differential value with respect to the search line direction, and proceeds to step 118. Step 118 makes a test to see if the differential values are calculated for all of the pixels of the search line segment PLj. If not, step 120 advances the current processing point by one pixel, i.e., proceeds to the next pixel of the line segment PLj. If the test result is YES in step 118, then step 122 makes another test to see if the pixel that has, in absolute value, the maximum differential value of all the pixels of the search line segment PLj is positive in the differential value thereof.

If so, it is determined that the pixel of the maximum differential value is suitable for the contour point. Thus, step 124 selects the pixel of the maximum differential value as the contour point, and proceeds to step 126. Step 126 makes a test to see if all of the contour points to be obtained in the search cycle i have been obtained, i.e., if the contour point counter j has reached the total number (Li) of the contour points to be obtained in the search cycle i. If not, then step 128 increments the j counter, and returns to step 106.

If the pixel of the maximum differential value is not positive in the differential value thereof in decision step 122, then it is determined that the pixel of the maximum differential value is not suitable for the contour point. This is because the judgement on the suitability of contour point according to the sign of the differential value of the contour point is based on the fact that, in an echo image in which an inner organ such as the heart, the prostate, etc. is shown, the distribution of pixel values near the border of the organ increases (or pixel values greatly change from dark to bright) in the outgoing direction; and the differential value in the outgoing direction along the search line segment PLj is positive and becomes the maximum near the contour line of the organ. For this reason, if the differential value of a pixel is negative, it may be said that a wrong position or pixel is probably selected due to the influence of noises, shadows, etc., causing it to be determined that the pixel is not suitable for the contour point. Thus, if the test result is NO in step 122, then the control is passed to step 136 to enter a process for the case of the negative differential value. FIG. 8 is diagrams showing the way of obtaining a suitable contour point when the contour point candidate is not suitable for the contour point in step 122.

Figure 8A:
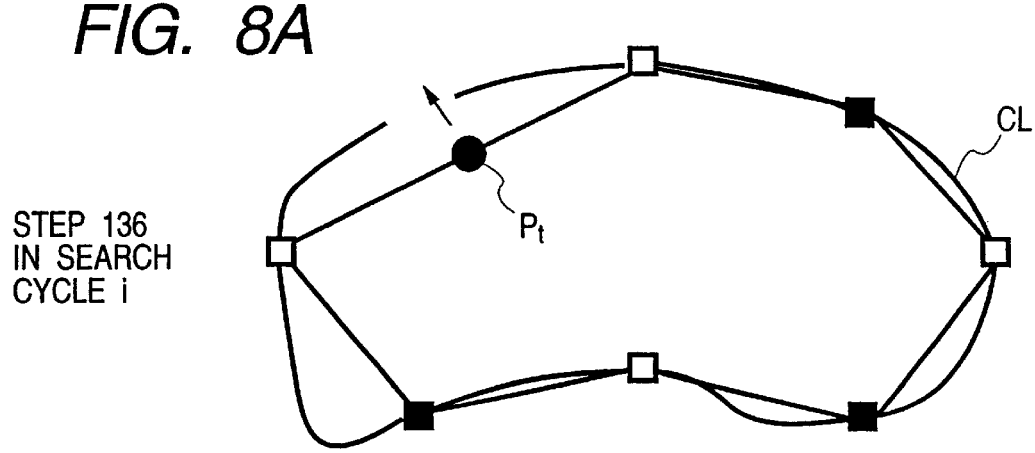
FIG. 8 is diagrams showing the way of obtaining a suitable contour point when the contour point candidate is not suitable for the contour point in step 122.
Figure 8B:
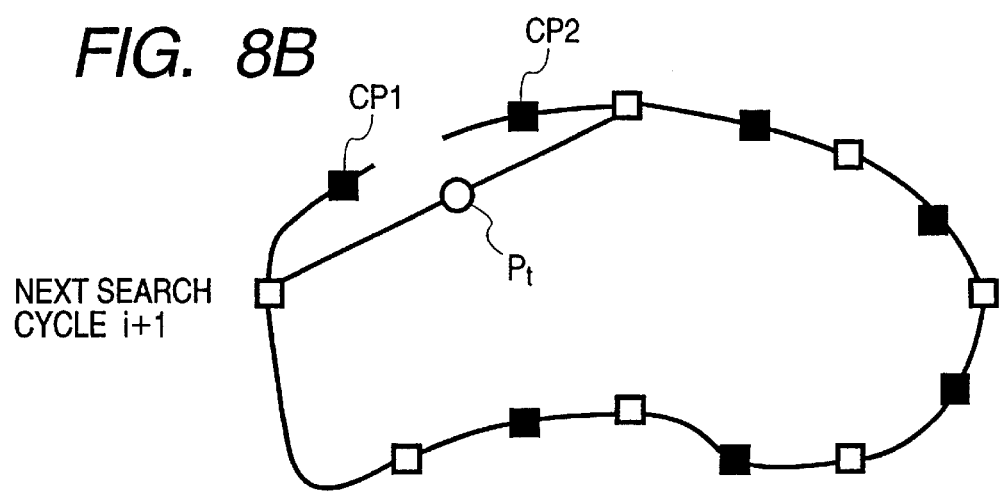
Figure 8C:
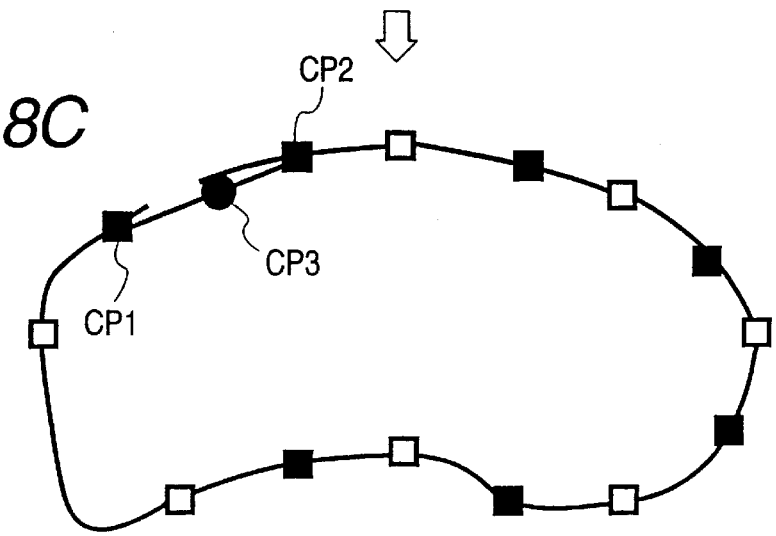

Step 136 selects the center between the adjacent reference points $P_{2j-1}$ and $P_{2j+1}$ as a temporary contour point in an i-th search cycle as shown in FIG. 8A. The center Pt is shown as a small circle filled with black in FIG. 8A. Then, the control is passed to step 138. Step 138 makes a test to see if all of the contour points to be obtained in the search cycle i have been obtained. If not, then step 128 again increments the j counter, and returns to step 106. If the result is YES in step 138, then the control is passed to step 140. If there is no temporary points obtained in the last search cycle (i−1), then step 140 simply proceeds to step 130. In the search cycle i+1, the temporary contour point Pt obtained in the i-th search cycle is used as a reference contour point to obtain two contour points (CP1 and CP2 in FIG. 8B) adjacent to the temporary contour point Pt. If there are any temporary points obtained in the last search cycle (i−1), then, for each of such temporary points, step 140 calculates a center point CP3 between the contour points CP1 and CP2 as a contour point as shown in FIG. 8C.

After step 140 or after a decision of YES in step 126, step 130 makes a test to see if all the search cycles have been completed, i.e., the search cycle counter i has reached a predetermined search cycle count L. If not, then step 132 increments the i counter, sets the j counter to one, and returns to step 106. If the i counter has reached the value L meaning the completion of all the search cycles, then the control is passed to step 134. Step 134 connects each adjacent pair of all the obtained contour points with a straight line or a spline curve to form a complete contour line. This step completes the operation of contour extraction of organ. The obtained contour line is used for a superimposition over a tomographic image. The obtained contour line is also used for the calculation of the section area, the girth, etc. of an inner organ.

According to the first illustrative embodiment of the invention, providing a step (107, 108) of limiting the area of search for a new contour point on the basis of reference or known contour points can reduce the possibility of putting out a wrong position as a contour point due to noises or a pixel distribution similar to the boundary of the organ. Also, the amount of processing is reduced by the limited amount of the search area.

Though differential values have been used for the decision of contour points on the search line segment, a value that has been weighted depending on the distance from the intersecting point of a connecting line between adjacent reference contour points and the search line may be used.

In the above-described embodiment, only one contour point has been obtained from two adjacent reference points. However, more than one contour point may be obtained from the two adjacent reference points.

Setting Three Initial Points

Figure 9:
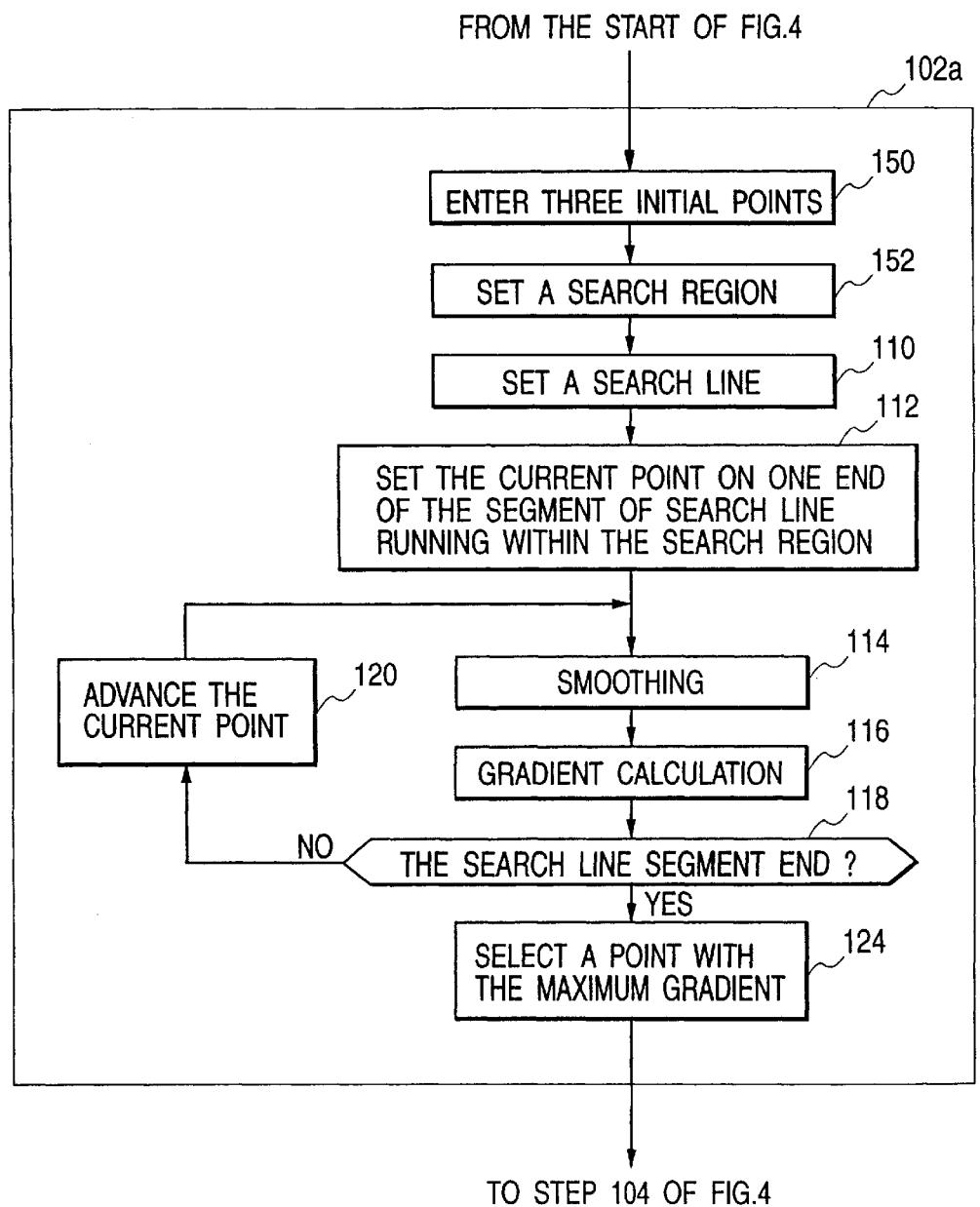
FIG. 9 is a flowchart showing a sequence 102a that can be executed instead of step 102 of FIG. 4 to let the user enter three initial points at the beginning of a contour extraction process.
Figure 10:
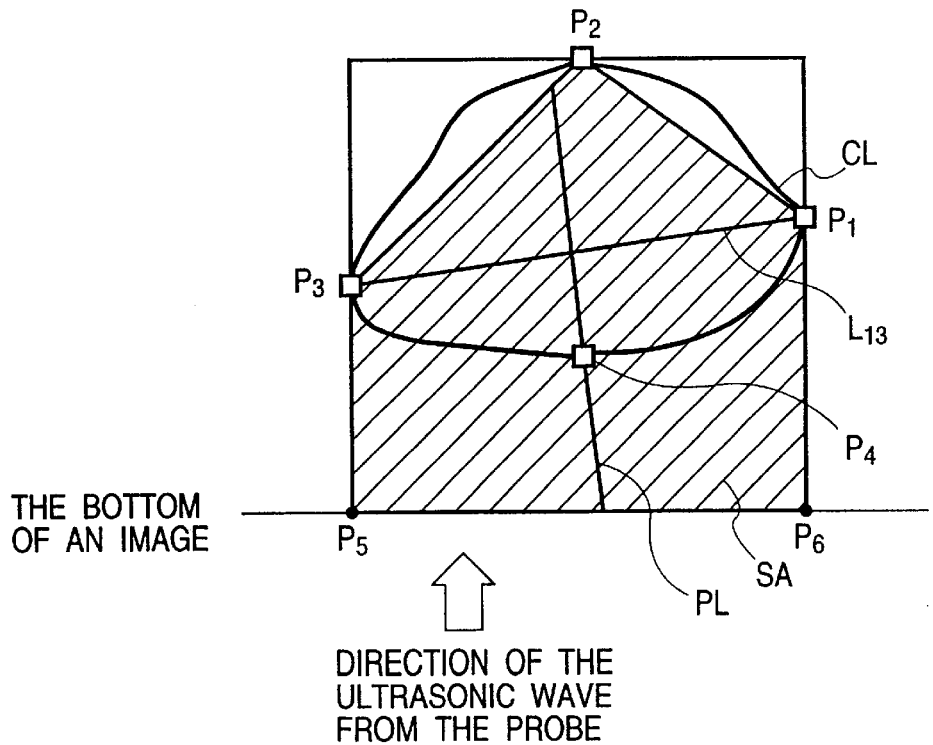
FIG. 10 is a diagram showing the way of setting three initial contour points and obtaining the fourth contour point.

FIG. 9 is a flowchart showing a sequence 102a that can be executed instead of step 102 of FIG. 4 to let the user enter three initial points at the beginning of a contour extraction process. FIG. 10 is a diagram showing the way of setting three initial contour points and obtaining the fourth contour point. In FIG. 9, step 150 lets the user enter three initial contour points P1, P2 and P3 substantially on the border CL of the organ as shown in FIG. 10. In this case, the three initial points are so selected that two of the three points, i.e., P1 and P3 are at the maximum distance in the direction substantially perpendicular to the direction of the ultrasonic wave from the probe 10; and the other point P2 is at the longest distance from the ultrasonic wave source or the ultrasonic probe 10. Though the first embodiment has used, as initial points, two points the furthest apart with other in the direction of the ultrasonic wave by also selecting a point nearest from the ultrasonic probe 10. However, a section of the organ border, which lies on the side nearer to the probe 10 and is substantially perpendicular to the direction of the ultrasonic wave is usually imaged more clearly in an ultrasonic tomographic image. In this case, an error will hardly occur in searching for a contour point even if the search area is enlarged by omitting an initial point nearest to the ultrasonic wave source.

Step 152 sets a search area (or region) in a manner unique to this step. Specifically, the search area SA (indicated as a shaded area) comprises a triangle P1, P2 and P3 and a trapezoid (P1, P3, P5 and P6) having, as sides thereof, a line segment P1–P3 and an image end (or the bottom) of the side of the ultrasonic wave source. After step 152, step 110 sets a search line segment PL which intersects substantially perpendicularly with the line L13 between the points P1 and P3 at the center of the line L13. Thereafter, steps 110 through 118 and 124 searches the search line segment PL for a contour point P4. Since four contour points have been obtained through the sequence 102a, the sequence 102a provides the same result as in case when step 102 is executed. Thereafter, the control is passed to step 104 of FIG. 4.

Since a contour section which is substantially perpendicular to the direction of the ultrasonic wave provide strong reflected waves and accordingly appears clearly in the echo image, an arrangement may be made, by omitting the point P2, such that only the points P1 and P3 are given as initial contour points.

If it is guaranteed that the target organ has a convex shape, then only the trapezoid (P1, P3, P5 and P6) may be used as the search area SA.

Calculation of the Area and the Volume

Figure 11:
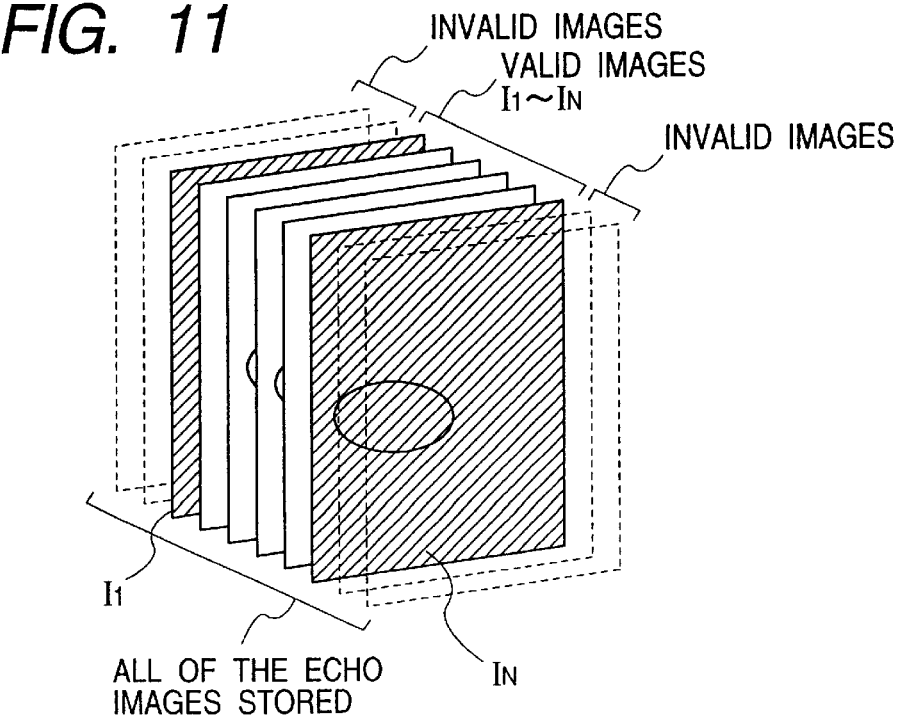
FIG. 11 is a diagram showing the echo images stored for an inner organ and used for the calculation of a section area and the volume of the organ in accordance with a second illustrative embodiment of the invention.

FIG. 11 is a diagram showing the echo images stored for an inner organ and used for the calculation of a section area and the volume of the organ in accordance with a second illustrative embodiment of the invention. In FIG. 11, the echo images are grouped into invalid images that contain no image of the organ and valid echo images I1 through IN (N is the number of the valid echo images) which contain images of the organ.

The echo images of FIG. 11 are obtained either by recording the echo images at respective slice positions parallelly arranged at a constant interval in the inner organ or by recording the echo images at respective slice positions radially arranged at a constant angular interval in the inner organ.

Figure 12:
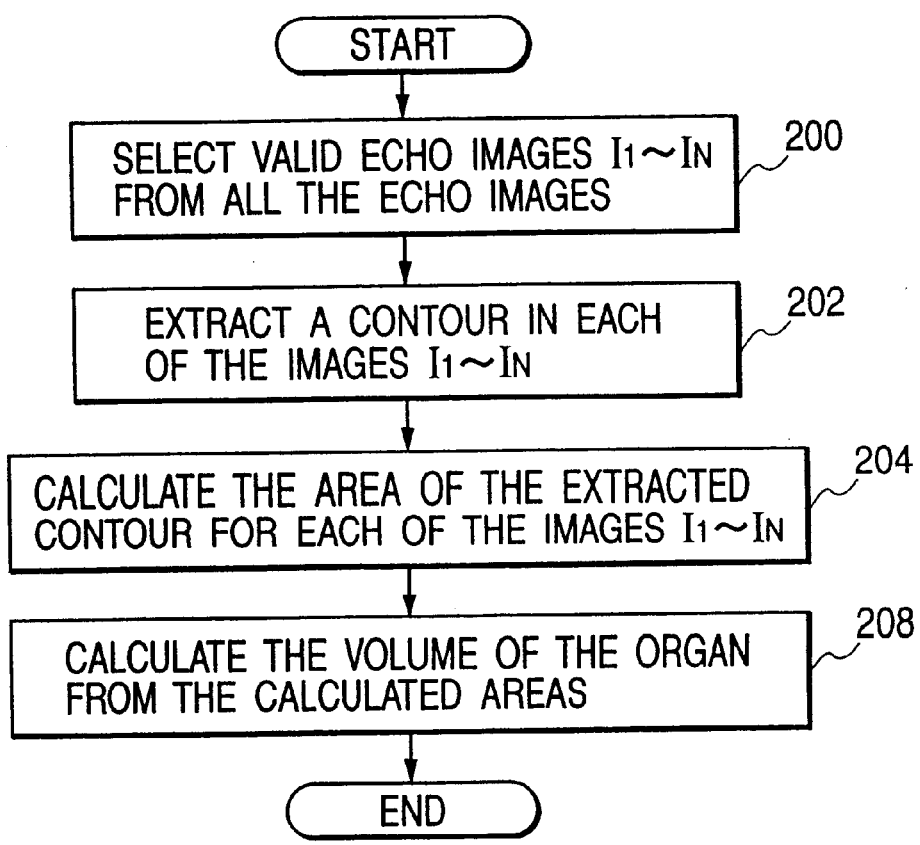
FIG. 12 is a flowchart showing a sequence of calculating an area and the volume of the inner organ from the echo images of FIG. 11.

FIG. 12 is a flowchart showing a sequence of calculating an area and the volume of the inner organ from the echo images of FIG. 11. In FIG. 12, step 200 selects valid echo images ($I_1$ through $I_N$) that contain any image of the internal organ from all of the echo images. N is the number of the valid echo images. Step 202 extracts a contour in each of the valid images $I_1$ through $I_N$. The contour extraction in step 202 is achieved in a manner described in the first illustrative embodiment of the invention.

Step 204 calculates the area of the extracted contour for each of the valid images $I_1$ through $I_N$, and proceeds to step

208. Step 208 calculates the volume of the organ. If the echo images have been obtained by recording them at respective slice positions parallelly arranged at a constant interval in the inner organ, then the calculation of the volume is achieved by summing a product of the calculated area of each valid image and the constant interval.

The extracted contours may be used for forming a three-dimensional model for 3D display instead of calculating the volume of an organ.

Though the volume of an organ is calculated by calculating the sectional area of each echo image, the surface area of the organ can be calculated by calculating the girth of each of the extracted contours.

Volume Calculation by Approximation

Figure 13:
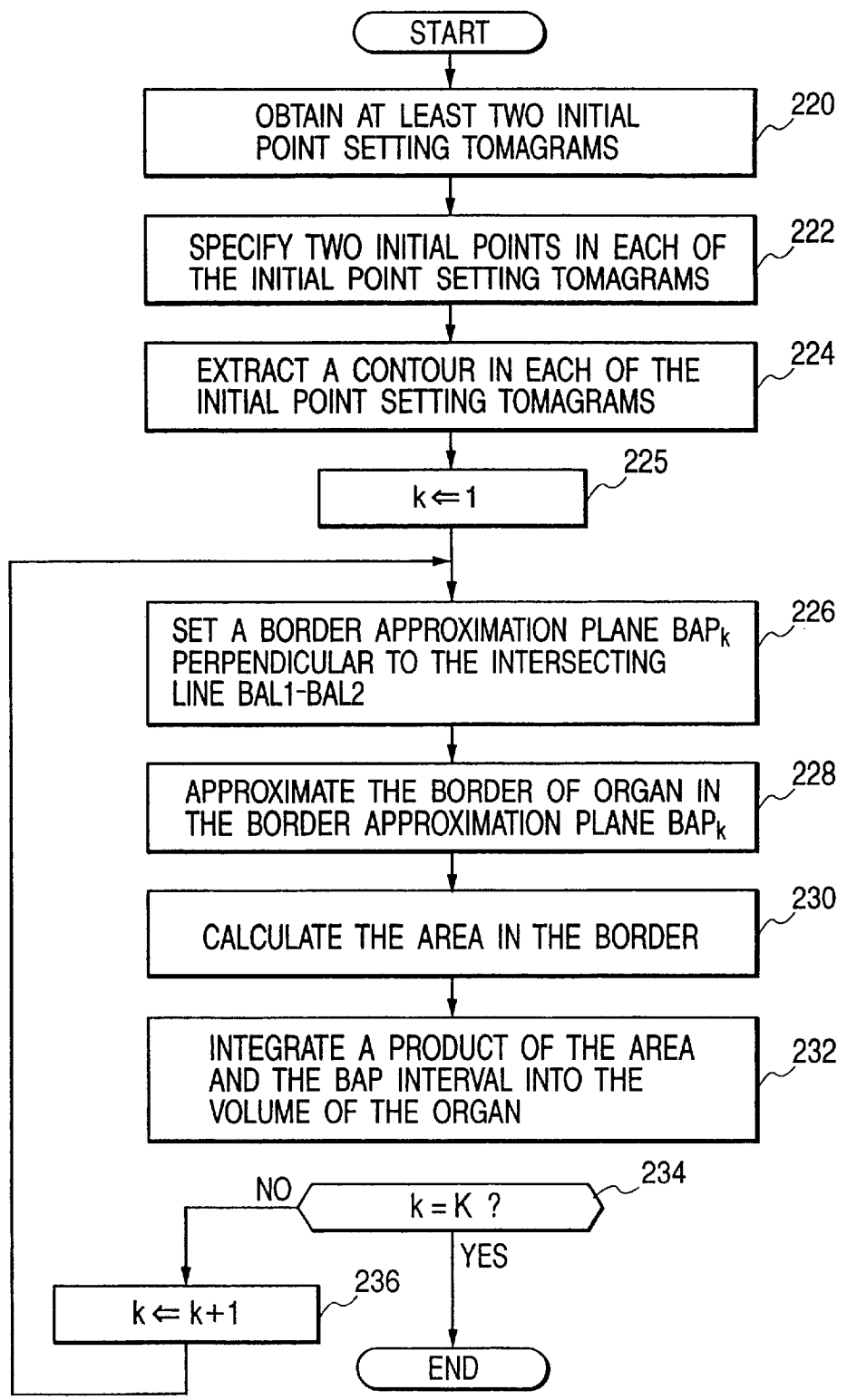
FIG. 13 is a flowchart showing a sequence executed by CPU 30 in calculating the volume of an internal organ by using two or more initial point setting tomograms and many approximation planes in accordance with a third illustrative embodiment of the invention.
Figure 14:
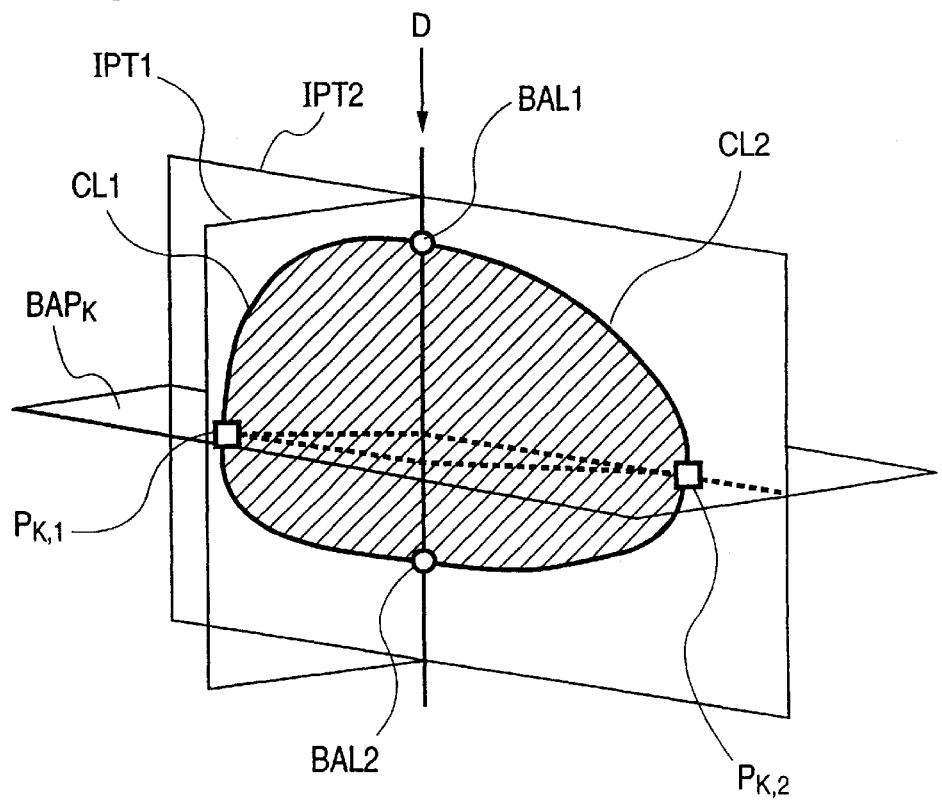
FIG. 14 is a diagram showing main tomograms used in the sequence of FIG. 12.

FIG. 13 is a flowchart showing a sequence executed by CPU 30 in calculating the volume of an internal organ by using two or more initial point setting tomograms and many approximation planes in accordance with a third illustrative embodiment of the invention. FIG. 14 is a diagram showing main tomograms used in the sequence of FIG. 12. A term "tomogram" means an echo image taken along a cross section of a body. In FIG. 13, step 220 first obtains at least two initial point setting tomograms, e.g., IPT1 and IPT2 as shown in FIG. 14. It is preferable that the two tomograms IPT1 and IPT2 are substantially perpendicular to each other and contain sections of an organ which sections have the maximum areas. In FIG. 14, the tomograms IPT1 and IPT2 contains organ sections defined by contours CL1 and CL2, respectively. The contours CL1 and CL2 intersects with each other at points BAL1 and BAL2 on the line of intersection of the tomograms IPT1 and IPT2.

Following step 220, step 222 permits the user to specify two initial contour points on each of the tomograms IPT1 and IPT2. Since intersecting points BAL1 and BAL2 already exist, the initial contour points are preferably so specified as to provide the length of the organ in the direction substantially perpendicular to the line BAL1–BAL2. Step 224 extracts contours CL1 and CL2 of the organ in respective tomograms IP1 and IP2 in a manner described in conjunction with the first embodiment, and proceeds to step 225. Step 225 sets a parameter k (detailed later) to an initial value of 1.

Figure 15:
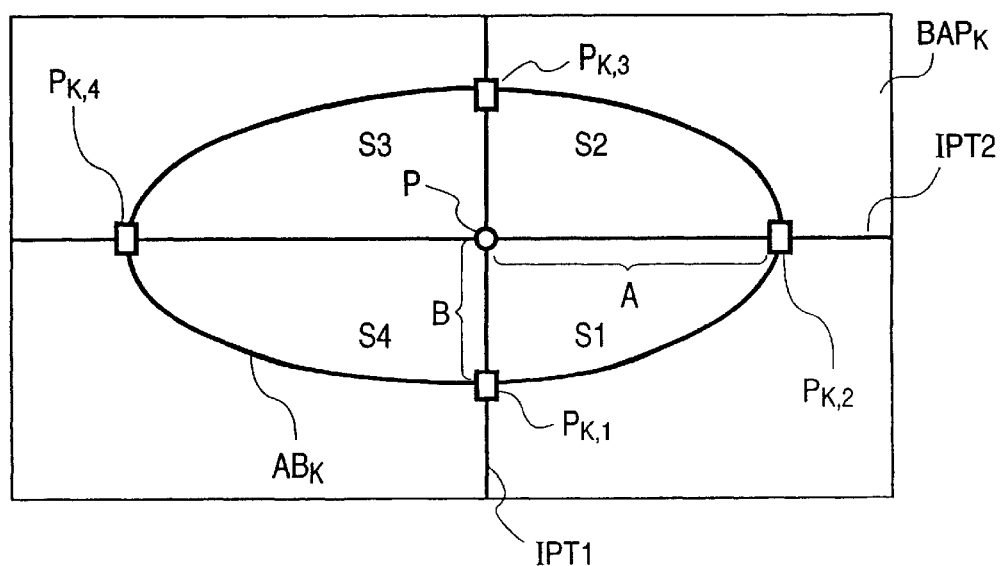
FIG. 15 is a diagram showing the border approximation plane BAPk of FIG. 14 viewed from the direction D shown in FIG. 14.

After step 225, step 226 sets a border approximation plane BAPk which is substantially perpendicular to the intersecting line BAL1–BAL2 in a range between the points BAL1 and BAL2, where k=1, 2, . . . , K, where K is the number of border approximation planes BAP1, BAP2, . . . , BAPK. The border approximation planes {BAPk: k=1~K} are preferably arranged at a constant interval in the range between BAL1 and BAL2. FIG. 15 is a diagram showing the border approximation plane BAPk of FIG. 14 viewed from the direction D shown in FIG. 14. In FIG. 15, a small circle denoted by "p" is an intersecting point made by the plane BAPk and the intersecting line by the initial point setting tomograms IPT1 and IPT2. The plane BAPk and the contour line CL1 on the initial point setting tomogram IPT1 makes two intersecting points $P_{k,1}$ and $P_{k,3}$. Similarly, the plane BAPk and the contour line CL2 on the tomogram IPT2 makes two intersecting points $P_{k,2}$ and $P_{k,4}$.

After step 226, step 228 generates a curve approximating the border of the organ in the border approximation plane BAPk set in step 226. If two initial point setting tomograms are used as shown in FIG. 14, the area containing an organ image is divided into four sections S1 through S4 as shown in FIG. 15. In this case, an approximation is performed in each of the four sections. In section S1 for example, an approximation is achieved by using the intersecting points P, $P_{k,1}$ and $P_{k,2}$ to finding an ellipse having a major axis A and a minor axis B, where A is the distance between the points P and $P_{k,2}$, and B is the distance between the points P and $P_{k,1}$. An approximated border on the plane BAPk is denoted by ABk in FIG. 15.

Step 230 calculates the area of the approximated border ABk by calculating the area of each of the sections S1 through S4. The area of Si is given by $$\frac{\pi}{4} * A * \frac{B}{4}.$$

Step 232 integrates a product of the area calculated in step 230 and the interval between tomograms to obtain the volume of the organ. Step 234 makes a test to see if the parameter k has reached the predetermined number K. If not, then step 236 increments k and returns to step 226. If the number K is reached in step 234, the operation is terminated.

As described above, the volume of an object is calculated from contours of the organ imaged in at least two tomograms by letting the user specifying two initial points on each tomogram, extracting a contour in each tomogram, setting border approximation planes and approximating the border of the organ, on each plane, by using four intersection points made by the plane and the extracted contours.

In the above description, the two initial point setting tomograms are perpendicular to each other, and the two tomogram and each approximation plane are set perpendicularly to each other. However, these tomograms and planes do not have to be strictly perpendicular. The tolerance in these angles may be determined according to the approximation accuracy.

There are a variety of combinations of the initial point setting tomograms. However, it is preferable to accord at least one tomogram with the scanning direction of the ultrasonic probe 10.

An ellipse approximation has been carried out by using two initial point setting tomograms in the above example. However, more precise approximation by spline interpolation is possible by using more than two initial point setting tomograms.

Though the volume of an organ is calculated by calculating the sectional area of each echo image, the surface area of the organ can be calculated by integrating the girth of each of the approximated borders.

Precise 3D Contour Extraction and Volume Calculation

Figure 16:
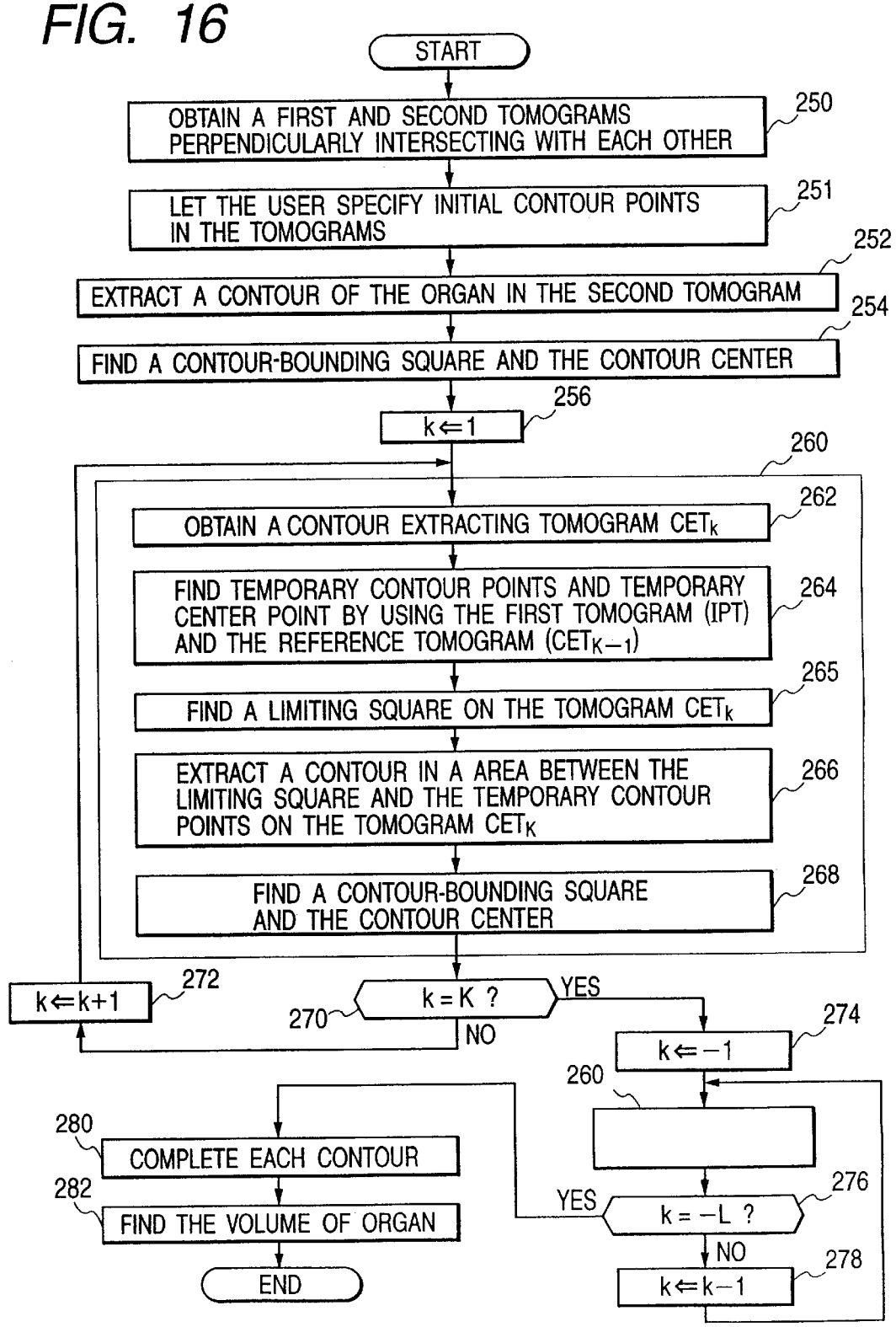
FIG. 16 is a flowchart showing a sequence executed by CPU 30 in calculating the volume of an internal organ by using two initial point setting tomograms and many contour extracting tomograms in accordance with a fourth illustrative embodiment of the invention.
Figure 17:
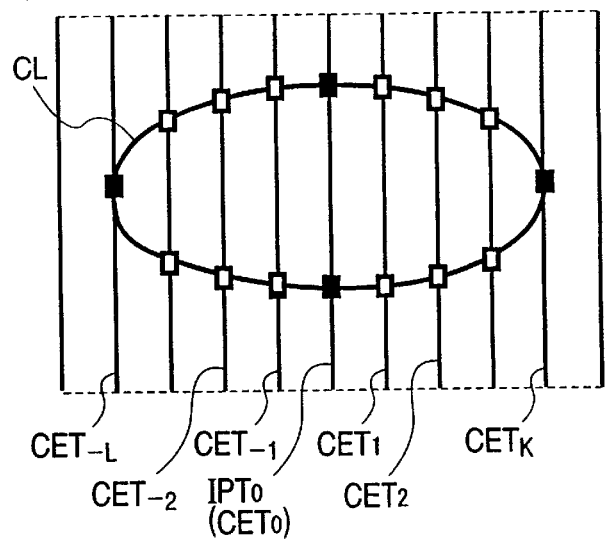
FIG. 17 shows a first initial point setting tomogram.
Figure 18:
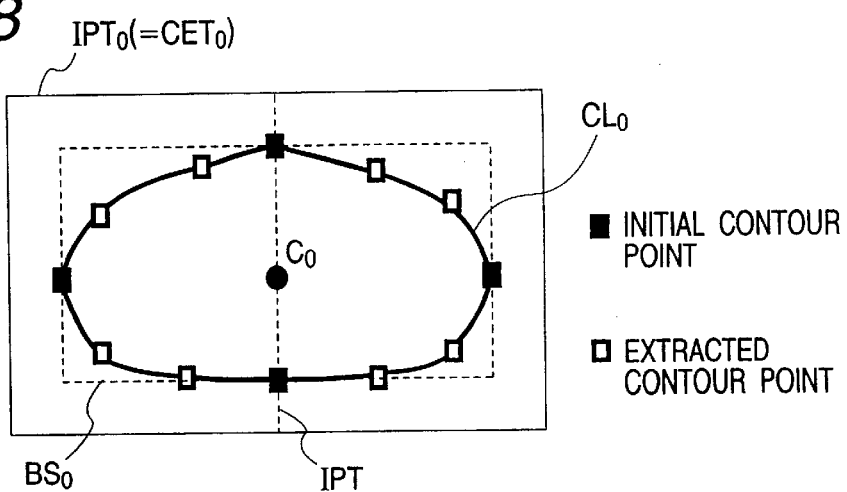
FIG. 18 shows a second initial point setting tomogram in which a contour of the organ is extracted based on initial points specified by the user.

FIG. 16 is a flowchart showing a sequence executed by CPU 30 in calculating the volume of an internal organ by using two initial point setting tomograms and many contour extracting tomograms in accordance with a fourth illustrative embodiment of the invention. FIGS. 17 and 18 show a first and a second initial point setting tomograms.

In FIG. 16, step 250 obtains a first and second initial point setting tomograms IPT and $IPT_0$ substantially perpendicularly intersecting with each other in almost center lines thereof. After step 250, step 251 lets the user specify initial contour points in the two tomograms IPT and $IPT_0$. Specifically, the user specifies two initial contour points on an intersecting line made by the two tomograms. The intersecting line is denoted by $IPT_0$ in FIG. 17 and by IPT in FIG. 18. The user further specifies two initial contour points in each of the two tomograms such that the distance between the two initial contour points substantially provides the length of the organ in the direction substantially perpendicular to the intersecting line. The initial points are shown as small squares filled with black in FIGS. 17 and 18.

After step 251, step 252 extracts a contour CL0 of the organ in the second tomogram $IPT_0$ based on the four initial contour points, i.e., two on the intersecting line IPT (shown vertically) and two providing a horizontal width as shown in FIG. 18. The extracted contour points are shown as small squares filled with white. Since a contour is extracted in the second tomogram $IPT_0$, the second tomogram $IPT_0$ is preferably disposed to accord with the scanning plane of the ultrasonic beam from the probe 10. Following step 252, step 254 finds a contour-bounding square $BS_0$ and the center $C_0$ of the contour CL0 as shown in FIG. 18. This completes the process concerning the second initial point setting tomogram $IPT_0$.

As shown in FIG. 17, many equally-spaced ultrasonic tomograms are taken parallel to the second initial point setting tomogram $IPT_0$ such that. Specifically, K contour-extraction tomograms $CET_1$, $CET_2$, ... and $CET_K$ are set on the right side of the second initial point setting tomogram $IPT_0$ (which can be said to be $CET_0$ in this sense). Similarly, L contour-extraction tomograms $CET_{-1}$, $CET_{-2}$, ... and $CET_{-L}$ are set on the left side of the second tomogram $IPT_0$ ($CET_0$). A contour of the organ is extracted in each of the K (or L) tomograms as detailed in conjunction with step 260.

In order to process the K tomograms to be disposed on the right side of $IPT_0$ or $CET_0$, step 256 sets the tomogram counter to 1, and proceeds to step 260, which begins with step 262. Step 262 obtains a contour extracting tomogram $CET_k$. If k=1 for example, then a tomogram $CET_1$ is taken disposed next to the reference or previous tomogram ($CET_0$ in this case) and a predetermined interval apart from the reference tomogram $CET_0$. In this way, the contour extracting tomograms are preferably processed sequentially from the second initial point setting tomogram $IPT_0$.

Figure 19:
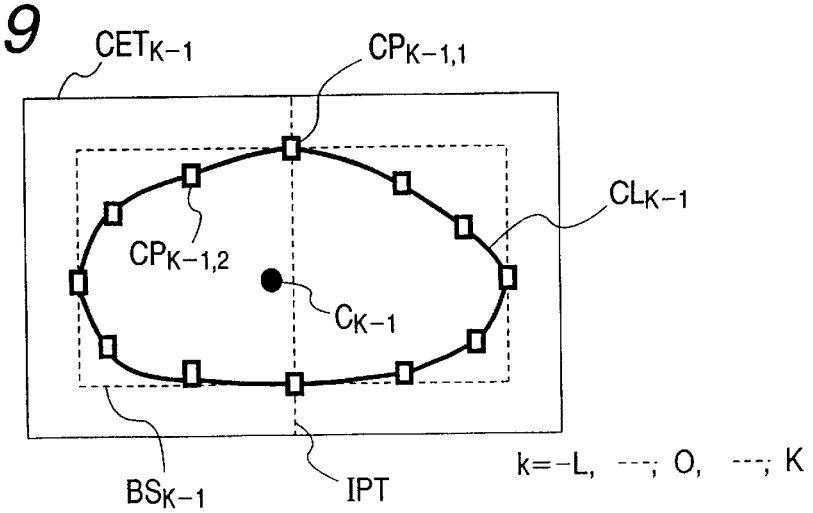
FIG. 19 shows a processed contour extracting tomogram $CET_k$ in which contour points and a center of an imaged border of the organ has been found.
Figure 21:
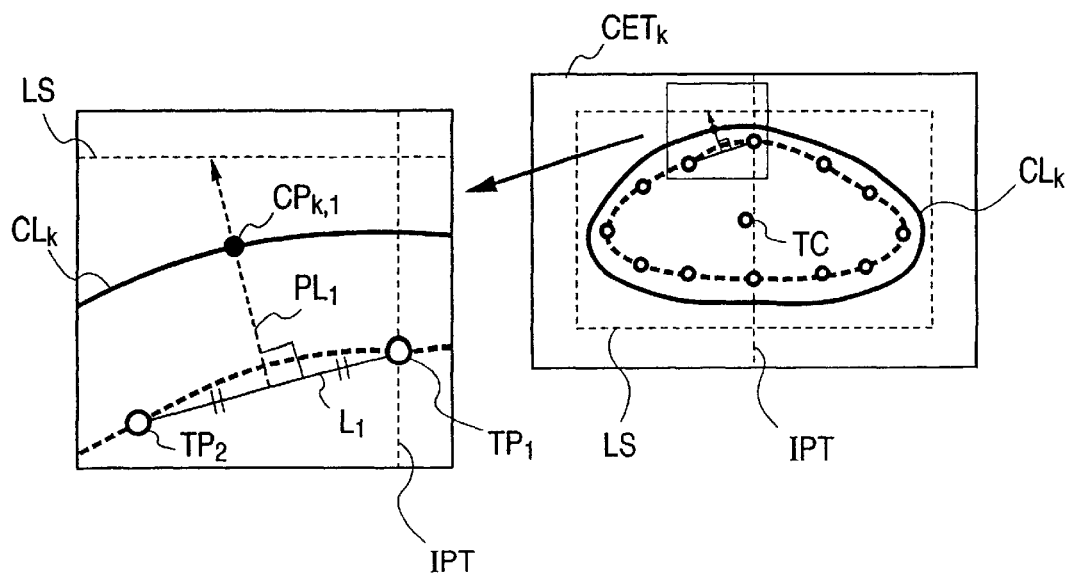
FIG. 21 illustrates how contour points and a center point of an imaged border of the organ is found in a contour extracting tomogram $CET_{k+1}$ disposed next to the tomogram $CET_k$ of FIG. 19.

In order to generalize the following description, it is assumed that contour extracting tomograms $CET_0$ through $CET_{k-1}$ ($-L+1<k<K+1$) has been processed and that contour points and a center of an imaged border of the organ are to be found in a next tomogram $CET_k$ ($1 \leq k$ is assumed, or $CET_{k-2}$ if k<1). FIGS. 19 and 21 are diagrams showing the tomogram $CET_{k+1}$ and $CET_k$. In FIG. 19, the contour points are denoted by $CP_{k-1,1}$, $CP_{k-1,2}$, ... The center or centered of the contour $CL_{k-1}$ is denoted by $C_{k-1}$. A square drawn by broken lines is a contour-bounding square $BS_{k-1}$, which shows ranges where the contour $CL_{k-1}$ exists.

Figure 20:
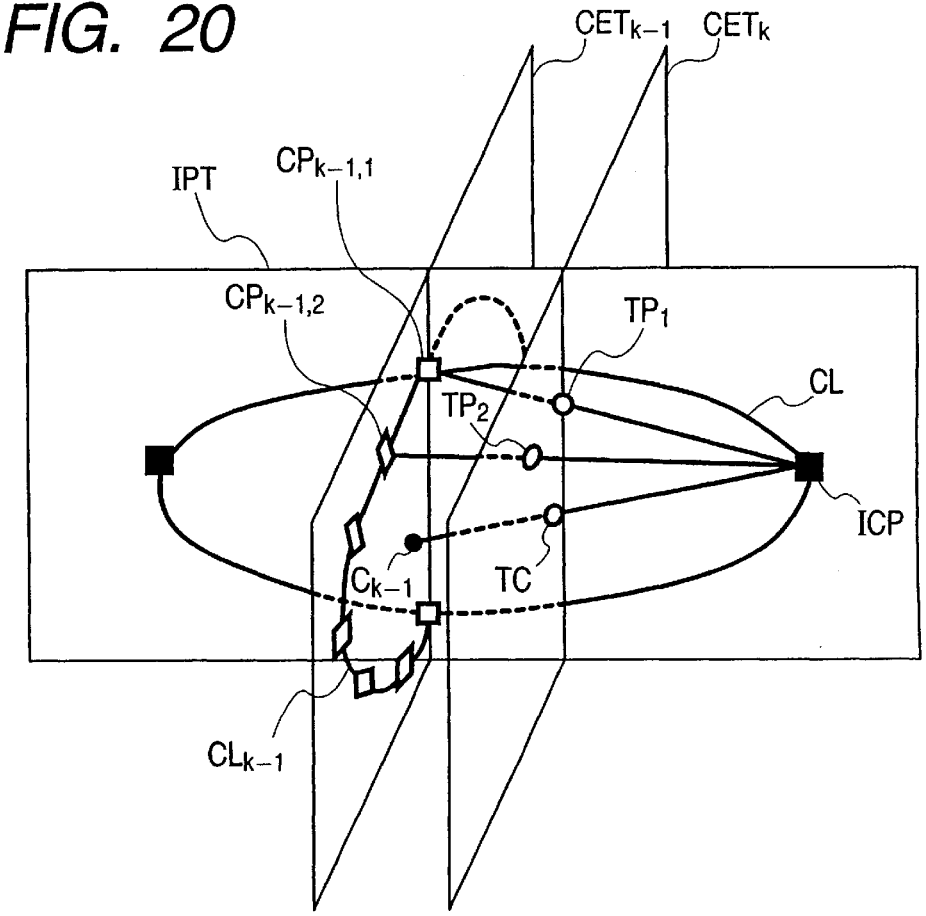
FIG. 20 illustrates how temporary contour points and a temporary center point in the tomogram $CET_{k+1}$ are estimated from the reference or previous tomogram $CET_k$ and the first initial point setting tomogram IPT.

After step 262, step 264 finds temporary contour points for the current tomogram $CET_k$ by using the first tomogram IPT and the reference or previous tomogram $CET_{k-1}$ as shown in FIG. 20. Specifically, in FIG. 20, lines are drawn from the rightmost initial contour point ICP to the contour points $CP_{k-1,1}$, $CP_{k-1,2}$, ... and the center $C_{k-1}$ on the tomogram $CET_{k-1}$ and the intersecting points made by the drawn lines and the tomogram $CET_k$ are made temporary contour points $TP_1$, $TP_2$, ... and a temporary center TC on the tomogram $CET_k$.

Step 265 finds a limiting square LS that limits the range of contour finding on the tomogram $CET_k$ by moving the contour-bounding square $BS_{k-1}$ on the previous tomogram $CET_{k-1}$ to the current tomogram $CET_k$ such that the center $C_{k-1}$ coincides with the temporary center TC.

It is noted that the size of the limiting square LS may be scaled in a range from 1 to 1.5 times in order to ensure finding a contour point on each search line segment (such as $PL_1$ of FIG. 21).

Step 266 extracts a contour in a area between the limiting square LS and the temporary contour points on the current tomogram $CET_k$. Specifically, each of adjacent temporary point pairs such as $TP_1$ and $TP_2$ are connected with a line segment (say, $L_1$ in this example). A search line segment ($PL_1$ in the example of FIG. 21) is so drawn as to perpendicularly bisect each of the drawn line segments and run from the drawn line to a side of the limiting square LS. Each of the search line segment $PL_1$ is searched for a contour point ($CP_{k,1}$ in the example of FIG. 21) in a manner described in the second illustrative embodiment. Thus, the contour points $CP_{k,1}$, $CP_{k,2}$, ... are obtained in the tomogram $CET_k$.

After step 266, step 268 finds a contour-bounding square (not shown) that defines a rectangular area where the contour points exist in the current tomogram $CET_k$. For the processing of the next contour-extracting tomogram $CET_{k+1}$, step 268 also finds a center (though not shown, it will be denoted by $C_k$) of the contour $CL_k$. The center Ck is determined either by calculating a centered or by finding an average of x-coordinates and an average of y-coordinates of the contour points.

Step 270 makes a test to see if the contour-extracting tomogram counter k has reached the predetermined number K. If not, then step 272 increments the counter k and returns to step 260 or 262.

If the result is YES in step 270, then step 274 sets the counter to −1 for processing the L contour-extracting tomograms on the left side of the second initial point setting tomogram $IPT_0$ or $CET_0$. Following step 274, CPU 30 executes the above-described routine 260. After routine 260, step 276 makes a test to see if the counter has reached a predetermined number −L. If not, then step 278 decrements the counter k and returns to the routine 260. If the counter k has reached −L, then step 280 completes a contour on each tomogram by connecting the obtained contour points. Finally, step 282 finds the volume of the organ in a manner described above.

In just described embodiment, the contour points are obtained from the temporary contour points. However, only two contour points providing a width and two contour points providing a height may be obtained from the corresponding temporary points, and the rest of the contour points may be obtained by using the four contour points as initial points as described in the first embodiment.

Many widely different embodiments of the present invention may be constructed without departing from the spirit and scope of the present invention. It should be understood that the present invention is not limited to the specific embodiments described in the specification, except as defined in the appended claims.

What is claimed is:

1. A method for obtaining an approximated three-dimensional contour and/or quantitative information from at least two echo images intersecting each other, the method including the steps of;

specifying two points that lie on an intersecting line made by said at least two echo images and on said contour;

specifying, on each echo image two contour points providing a maximum length in a direction perpendicular to said intersecting line;

extracting a contour of an organ in each echo image;

setting a plurality of equally-spaced border approximation planes perpendicular to said intersecting line;

approximating a border of said organ based on intersecting points made by each border approximation plane intersecting said intersecting line and said extracted contours;

calculating an area enclosed by each border; and calculating a volume of said organ by integrating a product of said area of each border and an interval between said border approximation planes;

wherein said at least two echo images comprises two echo images making an angle of 90 degrees and wherein said step of calculating an area enclosed by each border includes the step of calculating said area by calculating $$\left(\frac{\pi}{4}\right)*A*\left(\frac{B}{4}\right)$$

where A and B are the lengths of a major axis and a minor axis of each of four area divided by said two echo images.

2. A system as for obtaining an approximated three-dimensional contour and/or quantitative information from at least two echo images intersecting each other, the system including:

means for specifying two points that lie on an intersecting line made by said at least two echo images and on said contour;

means for specifying, on each image, two contour points providing a maximum length in a direction perpendicular to said intersecting line;

means for extracting a contour of said an organ in each echo image;

means for setting a plurality of equally-spaced border approximation planes perpendicular to said intersecting line;

means for approximating a border of said organ based on intersecting points made by each border approximation plane intersecting said intersecting line and said extracted contours;

means for calculating an area enclosed by each border; and means for calculating a volume of said organ by integrating a product of said-area of each border and an interval between said border approximation planes;

wherein said at least two echo images comprise two echo images making an angle of 90 degrees and wherein said means for calculating an area enclosed by each border includes means for calculating said area by calculating $$\left(\frac{\pi}{4}\right)*A*\left(\frac{B}{4}\right)$$

where A and B are the lengths of a major axis and a minor axis of each of four areas divided by said two echo images.

* * * * *

UNITED STATES PATENT AND TRADEMARK OFFICE
CERTIFICATE OF CORRECTION

PATENT NO. : 6,839,456 B2
DATED : January 4, 2005
INVENTOR(S) : Yoshito Touzawa et al.

It is certified that error appears in the above-identified patent and that said Letters Patent is hereby corrected as shown below:

Title page,
Item [75], Inventors, change first inventor's city from "Toyama" to -- "Kawazaki" --.

Column 13,
Line 1, change "comprises" to -- comprise --;
Line 4, change "area" to -- areas --.
Line 12, delete "as";
Line 22, delete "said".

Signed and Sealed this

Ninth Day of August, 2005

JON W. DUDAS
*Director of the United States Patent and Trademark Office*